United States Patent [19]

Shimizu et al.

[11] Patent Number: 5,357,294
[45] Date of Patent: Oct. 18, 1994

[54] METHOD FOR DISPLAYING OPTICAL PROPERTIES OF CORNEAS

[76] Inventors: Kimiya Shimizu, Suite 503, 9-6, Nishikubo 2-chome, Musashino-shi, Tokyo; Shunichi Tanaka, Suite 302, 9-8, Yushima 1-chome, Bunkyo-ku, Tokyo, both of Japan

[21] Appl. No.: 88,023

[22] Filed: Jul. 9, 1993

[30] Foreign Application Priority Data

Jul. 13, 1992 [JP] Japan .................................. 4-207030

[51] Int. Cl.$^5$ .............................................. A61B 3/107
[52] U.S. Cl. ...................... 351/212; 351/205; 351/221; 351/246
[58] Field of Search .................... 364/224.5, 922–922.4; 351/200, 205, 206, 211, 212, 221, 245, 246, 247

[56] References Cited

U.S. PATENT DOCUMENTS

| | | | |
|---|---|---|---|
| 4,863,260 | 9/1989 | Gersten et al. | 351/212 |
| 4,995,716 | 2/1991 | Warnicki et al. | 351/247 X |
| 5,110,200 | 5/1992 | Snook | 351/212 |
| 5,159,361 | 10/1992 | Cambier et al. | 351/212 |
| 5,214,456 | 5/1993 | Gersten | 351/212 |

Primary Examiner—William L. Sikes
Assistant Examiner—David R. Parsons
Attorney, Agent, or Firm—Lorusso & Loud

[57] ABSTRACT

A method for visually representing for easy analysis the relations between a plurality of cornea-operated patients' tendencies over time to astigmatism on the one hand, and the surgical techniques employed in the operations on the other. A plurality of diopter data matrices are generated about the multiple corneas having different conditions. An arithmetic mean value of each of the components constituting the data matrices is calculated so as to prepare a mean value matrix. A standard deviation of each of the components is calculated using the mean value matrix and the data matrices so as to prepare a standard deviation matrix. The mean value matrix and the standard deviation matrix are displayed in relevant positions on a cornea map using any of color pallets and graphic patterns associated with the arithmetic mean value and standard deviation of the components.

2 Claims, 9 Drawing Sheets

| | | | | | | | | |
|---|---|---|---|---|---|---|---|---|
| ▨ | ▨ | ☰ | | | | | | k |
| 1 | 2 | 3 | 4 | 5 | 6 | 7 | 8 | n |
| 40 | 41 | 42 | 43 | 44 | 45 | 46 | 47 | m |
| 0.5 | 1.0 | 1.5 | 2.0 | 2.5 | 3.0 | 3.5 | 4.0 | SD |

METHOD FOR DISPLAYING OPTICAL PROPERTIES OF CORNEAS

BACKGROUND OF THE INVENTION

1. Field of the Invention

The present invention relates to a method for displaying optical properties of corneas having been operated on.

2. Description of the Prior Art

The refractive powers of a plurality of parts of a cornea, i.e., the focal lengths thereof, are not uniform over the entire cornea. This gives rise to astigmatism. The refractive power of an entire object, i.e., its diopter, is expressed by the inverse number 1/f of the focal length f of the object. In corneal topography, the diopters of minute spots (areas) on the cornea of each patient are represented by color code or in a three-dimensional manner. Conventional corneal topography thus practiced is not good enough in representing and evaluating a large number of operated patients' tendencies of eyesight recovery or a particular patient's tendency of eyesight recovery over time following operation. As such, the conventional topography dealing with operated corneas is only an insufficient tool with which a medical professor illustratively gives post-operative explanations to interns.

SUMMARY OF THE INVENTION

It is therefore an object of the present invention to overcome the above and other deficiencies and disadvantages of the prior art and to provide a method for displaying in a two-dimensional manner the optical properties of a large number of post-operative patients' corneas so as to represent and evaluate clearly the patients' tendencies of eyesight recovery or a particular patient's tendency of eyesight recovery over time following the cornea operation, the method further serving to offer effective educational data for giving post-operative explanations to interns in ophthalmology.

In carrying out the invention and according to one aspect thereof, there is provided a method for displaying optical properties of corneas comprising the steps of: establishing a cornea map by dividing a cornea of a three-dimensional shape into a plurality of minute areas in a predetermined coordinate system; establishing a pseudo-two-dimensional position matrix corresponding to the minute areas and made of a plurality of components; having a cornea analyzer measure the optical properties of the minute areas to generate data matrices corresponding to the components constituting the position matrix; and displaying the data matrices in relevant positions on the cornea map using any of color pallets and graphic patterns associated with the data values involved. What characterizes the method is that it further comprises the steps of: generating a plurality of data matrices about a plurality of corneas having different conditions; calculating an arithmetic mean value of each of the components constituting the data matrices so as to prepare a mean value matrix; calculating a standard deviation of each of the components using the mean value matrix and the data matrices so as to prepare a standard deviation matrix; and displaying the mean value matrix and the standard deviation matrix in relevant positions on the cornea map using any of color pallets and graphic patterns associated with the standard deviation of each of the components.

The inventive method allows the optical properties of given corneas to be plotted on a cornea map, whereby an arithmetic mean value distribution chart of the properties covering the entire cornea is obtained using color pallets. In practice, such arithmetic mean value distribution charts are made of two groups of people: patients whose corneas were operated on, and comparative people who have normal eyesight. Comparing and studying the charts between these two groups of people provides a valuable evaluation of surgical techniques for later improvement. In addition, the arithmetic mean value distribution charts when compared and evaluated offer good post-operative explanations to the patients and their family members as well as to interns. Meanwhile, standard deviation matrix distribution charts are used to check if the data about minute areas of the cornea actually center on, or deviate from, the arithmetic mean values even though the mean values appear to be distributed stably and close to normal values.

For the same group of patients, both arithmetic mean value matrix distribution charts and standard deviation matrix distribution charts may be prepared over their cornea maps at regular intervals following the operations. The charts thus prepared show for evaluation purposes numerical changes in the patients' tendencies toward astigmatism over time.

These and other objects, features and advantages of the invention will become more apparent upon a reading of the following description and appended drawings.

DESCRIPTION OF THE PREFERRED EMBODIMENT

Figure 1:
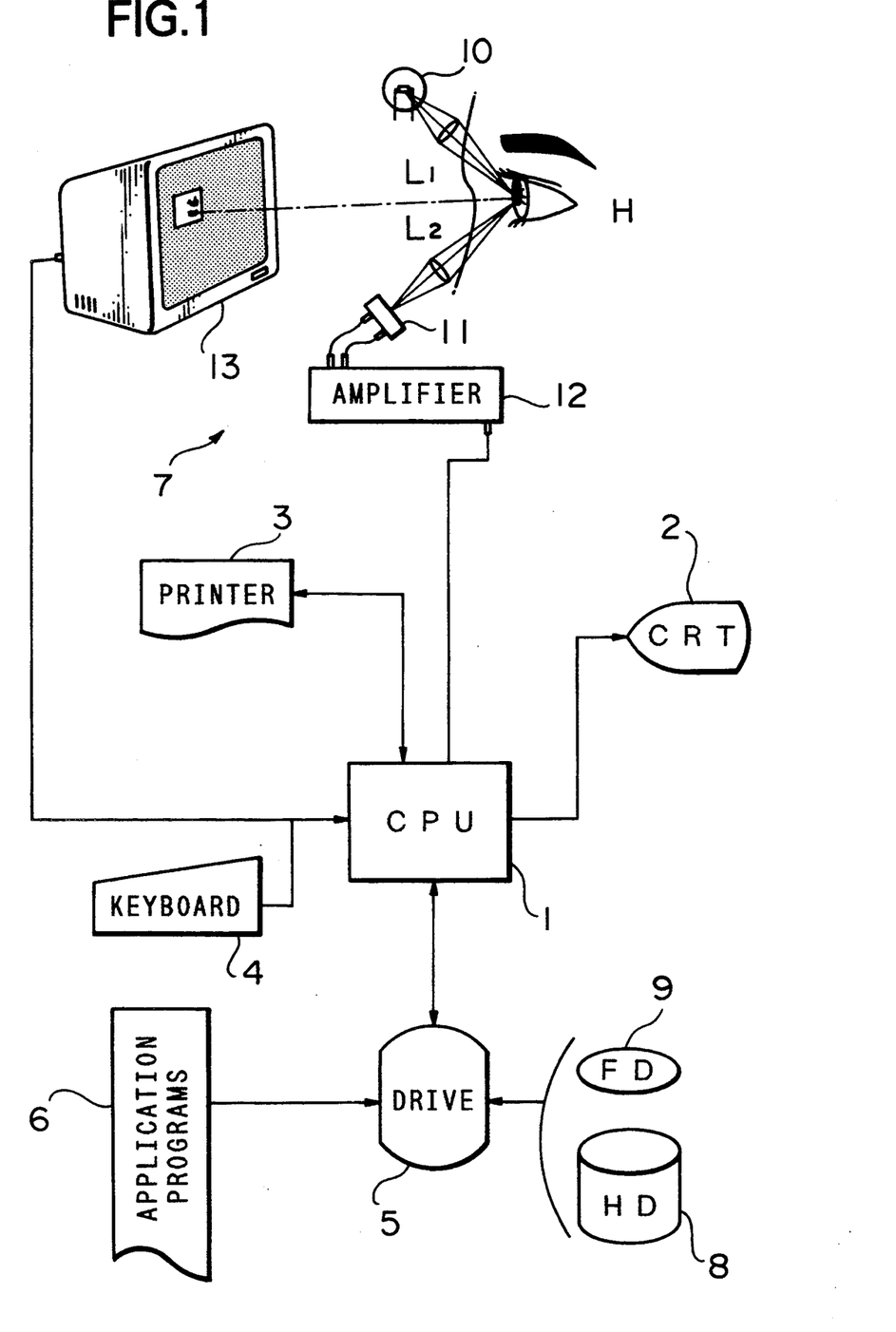
FIG. 1 is a block diagram of a data processor to which the embodiment is applied.

The invention will now be described with reference to the accompanying drawings. FIG. 1 is an overall block diagram of data processor hardware to which the invention is applied. In FIG. 1, a CPU (central processing unit) 1 is connected to a CRT 2, a printer 3, a keyboard 4, a driver 5 and a cornea analyzer 7. The driver 5 drives a hard disc 8 and a floppy disc 9 in a magnetic recording device. Application programs 6 are loaded through, say, the floppy disk 9 into the CPU 1. The application programs 6 include those for defining matrices as well as for calculating the arithmetic mean value and standard deviation of each of the components constituting the matrices. The cornea analyzer 7 is composed of a stare monitor 13, a light source 10, lenses L1 and L2, a measuring instrument 11 and an amplifier 12.

Figure 2:
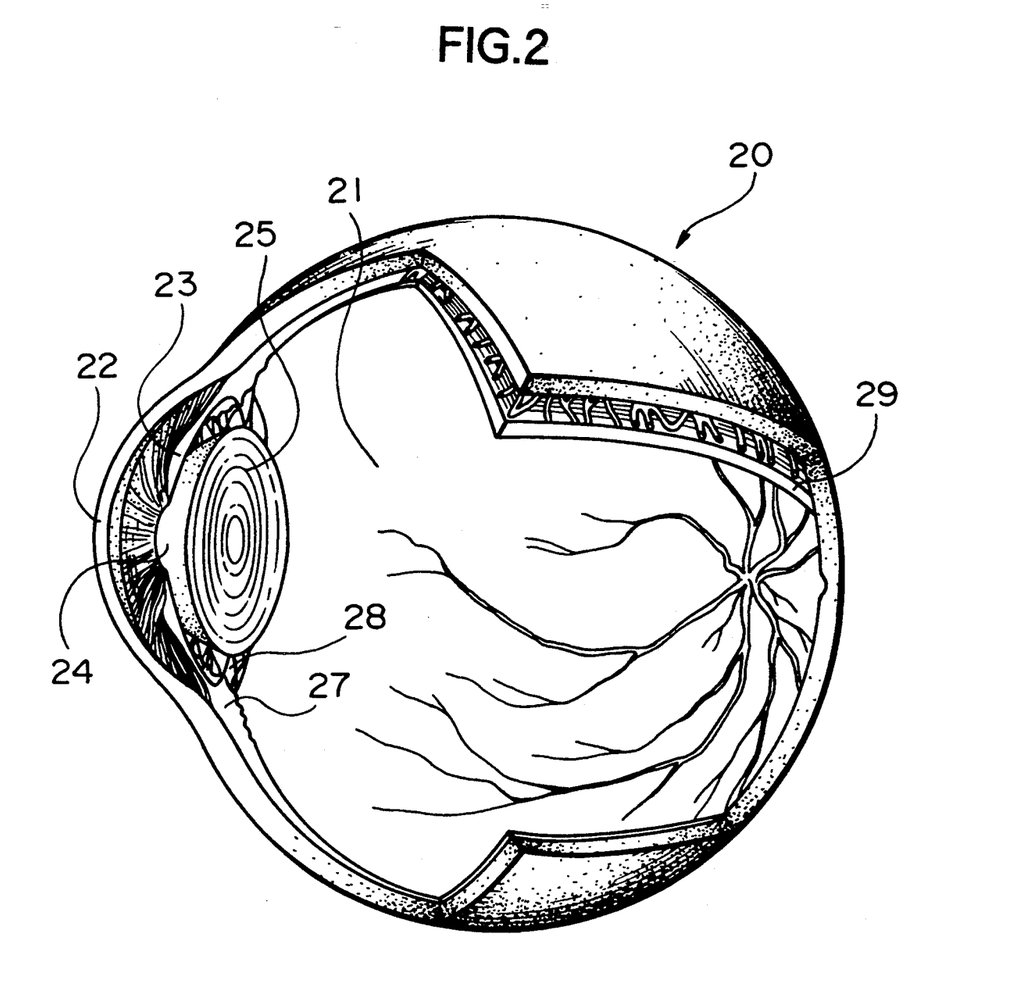
FIG. 2 is a view showing the structure of a human eye to which the embodiment is applied.

FIG. 2 shows the structure of a human eye. An eyeball 20 is 23 to 24 mm in diameter and is filled with a vitreous body 21. The topmost surface of the eye is a transparent cornea 22 followed by an iris 23, a pupil 24 and a crystalline lens 25, in that order. The lens 25 is varied in thickness by ciliary muscles 27 and suspensory ligaments 28 changing their tension. The light passing through the pupil 24 is focused on a retina 29 inside the eyeball 20. The refractive index of the cornea 22 is 1.38 compared with 1.0 of the air. The incident light entering the protruding cornea 22 is refracted before getting focused on the retina 29. Since the refraction by the cornea 22 alone is not enough for an image of an external object to be formed properly on the retina 29, the crystalline lens 25 is varied in thickness and the focal length thereof is adjusted accordingly. This allows the image of the external object to be formed precisely on the retina 29.

The cornea 22 can be clouded by trauma or through aging. A clouded cornea 22 causes irregular reflection preventing light from normally entering the crystalline lens 25. In that case, the cornea 22 is operated on for eyesight recovery.

Figure 3:
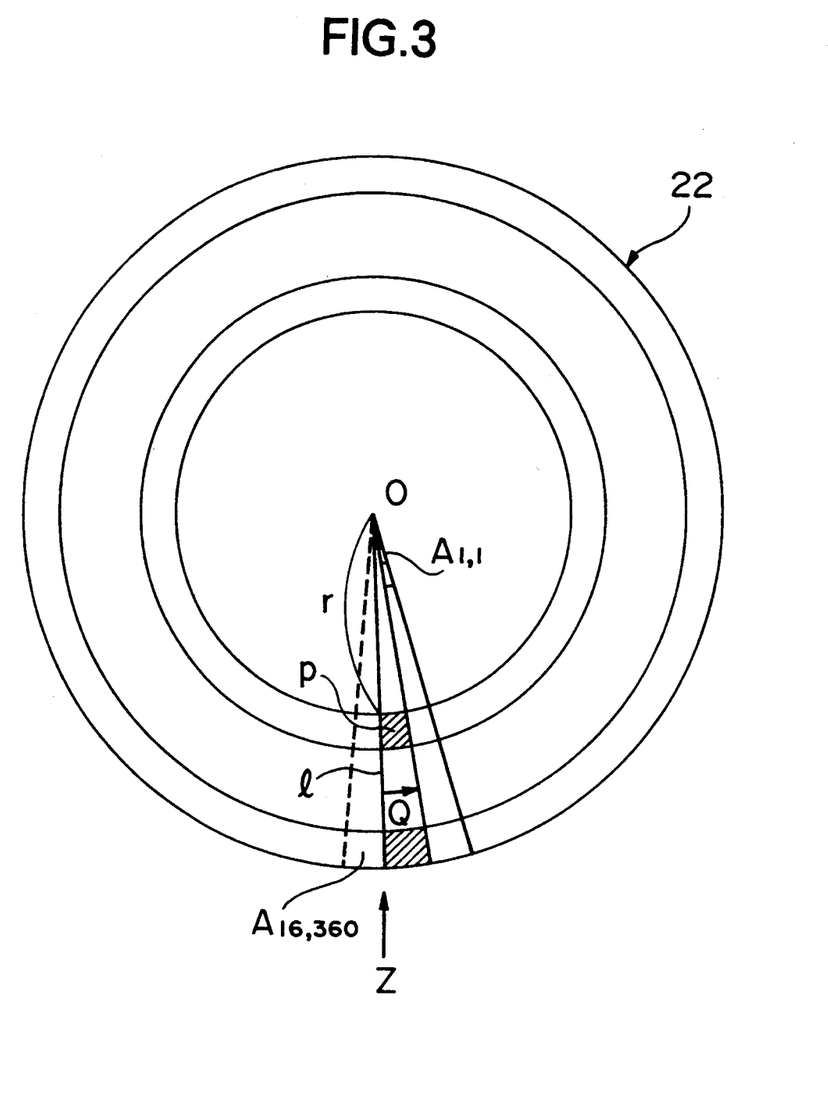
FIG. 3 is a view of a typical cornea map according to the invention.

FIG. 3 shows a typical cornea map prepared on a virtual basis by viewing the cornea 22 from the front Z. With the reference Z taken immediately below the front of the eyeball 20, the distance (radius) r with respect to the center O and an angular coordinate Q relative to a base line 1 are used to represent a cornea map as a set of minute points (or small areas, to be more precise) p. For example, the distance r is divided into 16 equal parts of the radius, and the angle Q is expressed in units of degrees. Then the cornea 22 is represented by a set of points p ranging from an inner annulus (A1, 1) to an outer annulus (A16, 360). The cornea map may also be established in any other appropriate coordinate system.

The points p may be arranged in the ascending order of the numbers attached thereto, as shown in Table 1 below.

TABLE 1

| A1, 1   | A2, 1   | A3, 1   | ... A16, 1   |
|---------|---------|---------|--------------|
| A1, 2   | A2, 2   | A3, 2   | ... A16, 2   |
| .       |         |         |              |
| .       |         |         |              |
| A1, 360 | A2, 360 | A3, 360 | ... A16, 360 |

Although the numbers of the points p from (A1, 1) to (A16, 360) are arranged sequentially in Table 1, the points in fact constitute annuli that spread outward from the center like the rings of a tree, as depicted in FIG. 3. This kind of polar coordinate system is used frequently in the field of topography.

When divided as described, one cornea 22 forms a position matrix composed of 5,760 points p (16×360) as illustrated in Table 2 below.

TABLE 2

| 1     | 2     | 3     | ... 16    |
|-------|-------|-------|-----------|
| 17    | 18    | 19    | ... 32    |
| .     |       |       |           |
| .     |       |       |           |
| 5,745 | 5,746 | 5,747 | ... 5,760 |

Each of the components for the points (A1, 1) through (A16, 360) in Table 1 is expressed as a matrix [Aij] of 360 rows and 16 columns.

The cornea analyzer of FIG. 1 is used to measure the optical properties of each of these 5,760 points p on each patient's cornea. Because optical properties correspond to diopters, i.e., to focal lengths, the CPU 1 measures the focal length of each of the 5,760 points p. The measurements are converted from analog to digital format before being placed into a RAM by the CPU 1. Executing an inverse number calculation program (one of the application programs 6), the CPU 1 then finds the inverse number of each focal length whereby the diopter of the current point is obtained. The diopters thus obtained are stored on the hard disc 8.

Because the focal lengths of the points p on the cornea 22 are mostly close to the retina 29, the focal points f are 0.023 to 0.024 meters around the radius of the eyeball. The inverse numbers of these focal lengths (1/f; diopters) are 1/0.024 to 1/0.023, i.e., 41 to 44. The more constant the diopters, the healthier the patient. Larger dispersions in diopters point to higher tendencies to astigmatism.

The measurements obtained from the cornea operation on a first patient provide diopters that are defined as a medical record comprising 5,760 data items, as shown in Table 3 below. The medical record is stored on the hard disc 8. The data in Table 3 are typical values shown for illustrative purposes. The medical record containing the measurements may be defined as a data matrix.

TABLE 3

| 40 | 41 | 42 | 43 |
|----|----|----|----|
| 44 | 45 | 46 | 47 |
| .  |    |    |    |
| .  |    |    |    |
| 43 | 42 |    | 41 |

Other patients who underwent the cornea operation are measured in like manner. When medical records of N patients have been thus prepared, they constitute a medical record file 31 of FIG. 4 wherein the records for first, second and Nth patients are illustrated.

One point p does not strictly correspond to one focal length f; a plurality of focal lengths f may sometimes be obtained for a single point p. For example, measuring the point p in the coordinate position (A1, 1) of the first patient may yield two focal lengths f, 0.023 and 0.025 meters. Each of the 5,760 points is measured to see how many samples were taken from the same point. The results are arranged into and defined as a sample count matrix H[ij] as shown in Table 4 below. This matrix is also stored on the hard disc 8.

TABLE 4

| 4 | 1 | 2 | 3 |
|---|---|---|---|
| 1 | 5 | 4 | 7 |
| . |   |   |   |

TABLE 4-continued

| 3 | 2 | 8 |
|---|---|---|

Figure 4:
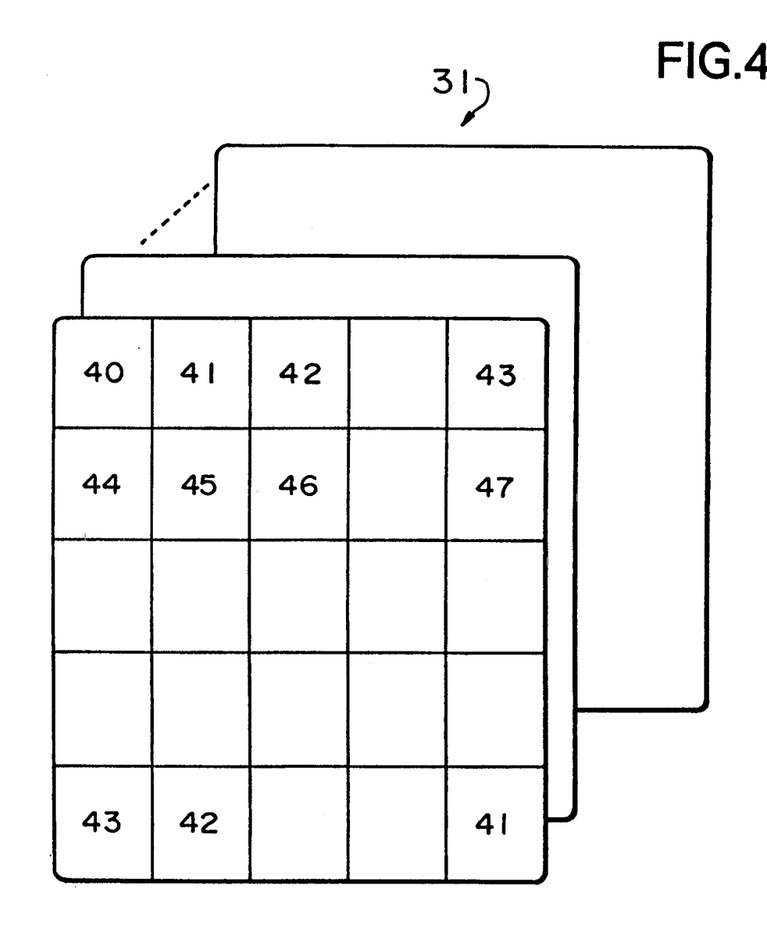
FIG. 4 is a view depicting typical medical record files in connection with the invention.

How many samples exist for each of the points involved varies from patient to patient. Thus the sample count matrix H[ij] of Table 4 needs to be measured and recorded for each of the patients, as is the case with the medical record file 31. The data items in the medical record file 31 of FIG. 4 represent each of the components constituting the point p matrix [Aij] of the cornea. The data items are defined as a diopter data matrix [Dij]. The medical record file 31 for N patients comprises N diopter data matrices [Dij] which are stored on the hard disc 8.

For each of the components of N data matrices [Dij], the CPU 1 calculates an arithmetic mean value $\Sigma Dij/N$. This provides a mean value matrix of Table 5 below. .pa

TABLE 5

| 40+41.../N | 40+41.../N | 40+41.../N | 40+41.../N |
|---|---|---|---|
| 40+41.../N | 40+41.../N | 40+41.../N | 40+41.../N |
| 40+41.../N | 40+41.../N | 40+41.../N | 40+41.../N |

In Table 5, the arithmetic mean value $\Sigma Dij/N$ is indicated for each component in the form of an arithmetic expression. On the hard disc 8, however, the mean value matrix $\Sigma[Dij/N]$ is stored in the form of values such as those listed in Table 3.

For each of the components constituting N sample count matrices H[ij], the CPU 1 calculates the arithmetic mean value $\Sigma Hij/N$. This provides a single sample mean value matrix $\Sigma[Hij/N]$ of Table 6 below.

TABLE 6

| 4+1.../N | 1+1.../N | 2+5.../N | 3+1.../N |
|---|---|---|---|
| 1+1.../N | 5+1.../N | 4+6.../N | 7+4.../N |
| . | | | |
| . | | | |
| . | | | |
| 3+1.../N | 2+8.../N | | 8+1.../N |

In Table 6, the arithmetic mean value $\Sigma Hij/N$ is indicated for each component in the form of an arithmetic expression. On the hard disc 8, however, the sample mean value matrix $\Sigma[Hij/N]$ is stored in the form of values such as those listed in Table 4.

Figure 5:
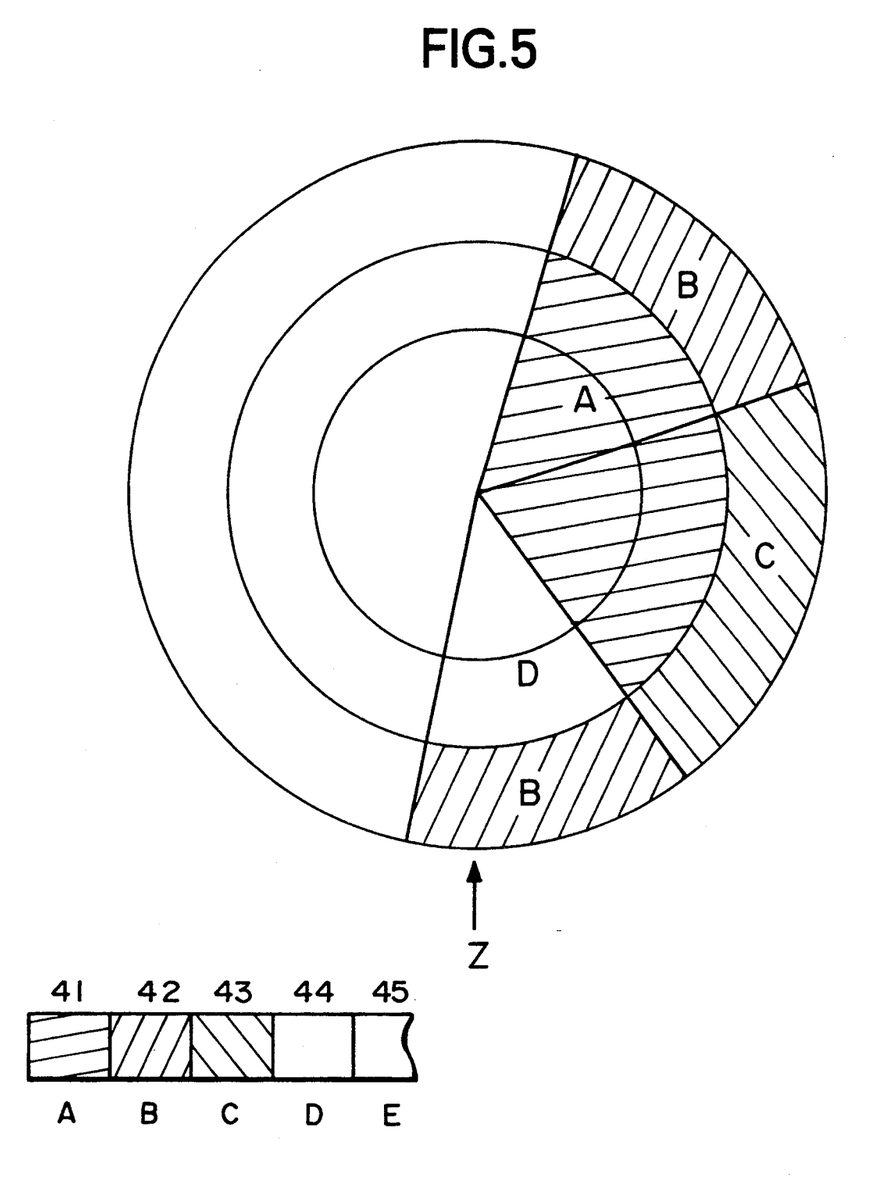
FIG. 5 is a distribution chart showing a mean value matrix using color pallets according to the invention.

Using color pallets, the CPU 1 then expresses the diopter mean value matrix $\Sigma[Dij/N]$ on the cornea map of FIG. 3, as shown in FIG. 5. The representation is given in color on the CRT 3. In FIG. 5, individual mean diopter values are shown in different colors: value 41 in color code A, value 42 in color code B, value 43 in color code C, value 44 in color code D, value 45 in color code E, and so on. Although the mean diopter values are given here as integers for the sake of simplicity, these values may alternatively be expressed in smaller units with fractions, e.g., 41.1, 41.2, etc. using an increased number of color pallets.

In this manner, an overall mean diopter distribution chart such as one in FIG. 5 is obtained over the cornea map of FIG. 3. The entire cornea map is to be covered with the distribution chart, although FIG. 5 shows only half of the chart together with color pallets.

Using color pallets, the CPU 1 then displays on the cornea map of FIG. 3 each patient's sample count matrix H[ij] and a sample mean value matrix for a given group of patients. This provides a sample count distribution chart and a sample mean value distribution chart in the form of the mean diopter distribution chart of FIG. 5.

Figure 6:
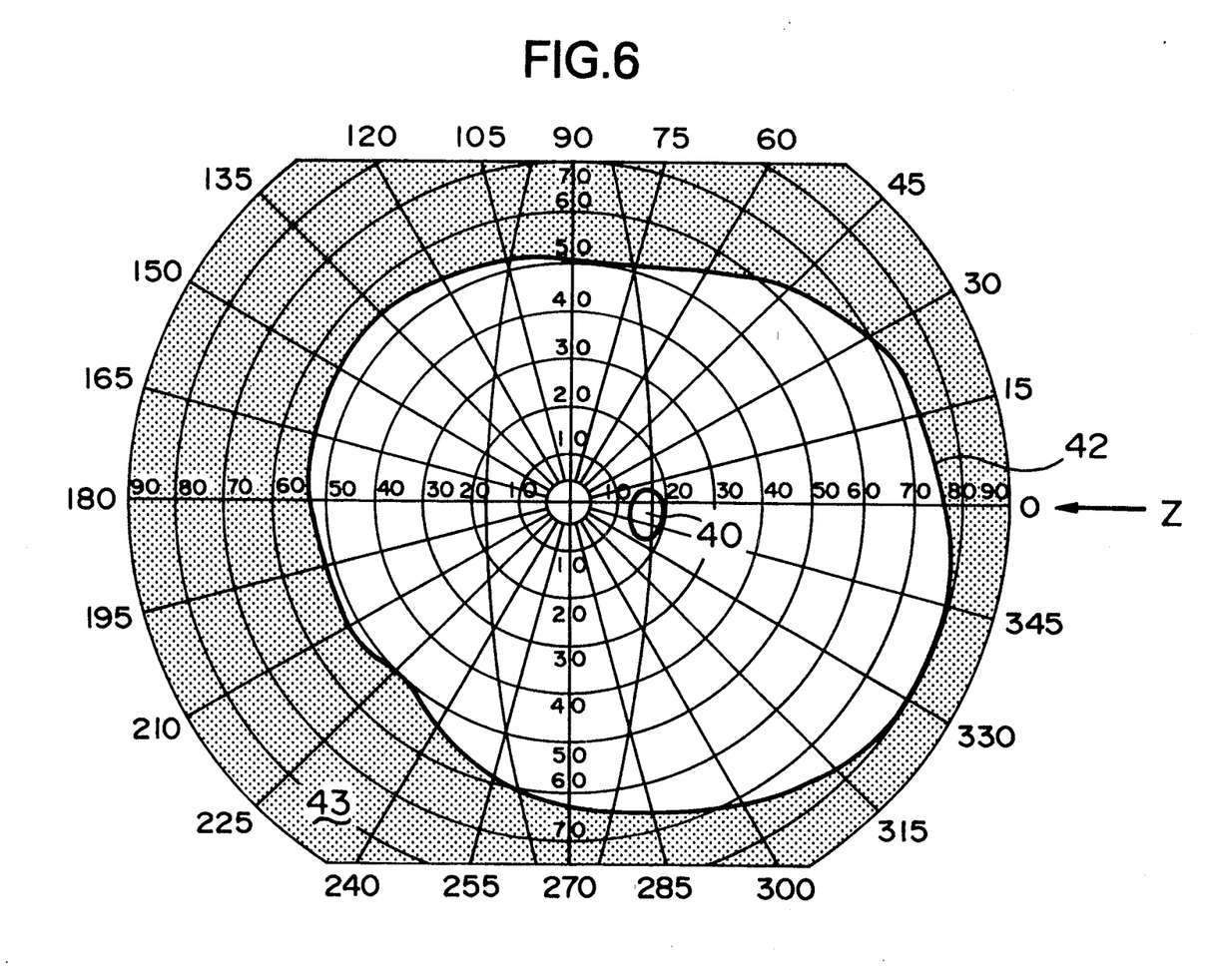
FIG. 6 is a view giving a mean value matrix distribution chart representing a group of operated patients.
Figure 7:
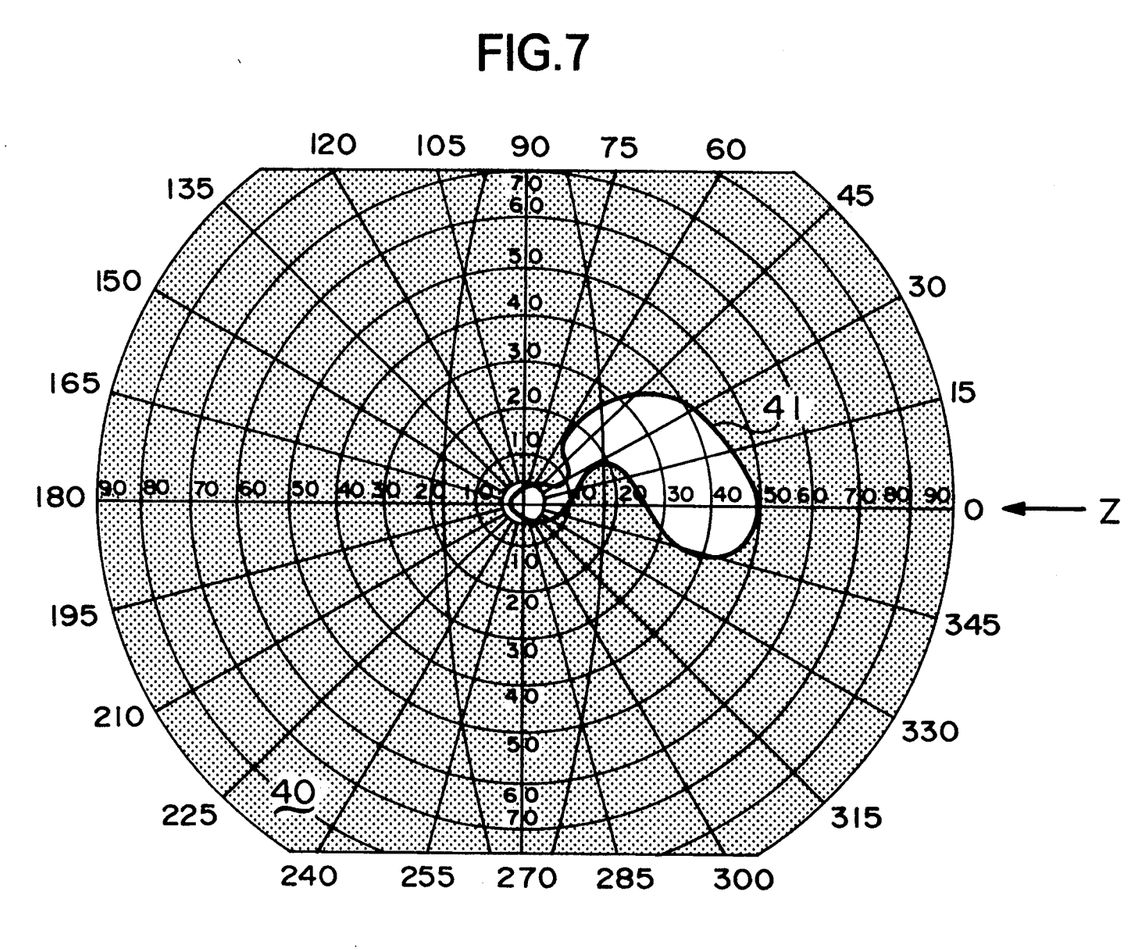
FIG. 7 is a view giving a mean value matrix distribution chart representing a group of people with normal eyesight.

As opposed to the group of patients having undergone the cornea operations, a group of people with twenty-twenty vision are examined and their medical records are obtained. An overall mean diopter distribution chart is then prepared from the medical records of these ophthalmologically normal people. This typically provides two mean diopter matrix distribution charts in FIG. 6 for comparison. The chart of FIG. 6 is an overall mean diopter distribution chart representing the group of operated patients; the other chart of FIG. 7 is an overall mean diopter distribution chart covering the group of people with normal eyesight. Comparing the two charts provides a valuable evaluation of the surgical techniques employed for later improvement. In addition, the comparative evaluation based on the mean diopter distribution charts serves to offer good post-operative explanations to the patients and their family members as well as to interns.

The same cornea-operated patients may be divided temporally into a number of groups, i.e., according to the elapsed time following the operation, and a mean diopter distribution chart may be prepared for each of such groups. Typically, the patients are divided into a group of patients operated on the day before, a group of patients operated on one week ago, a group of patients operated on one month ago, and a group of patients operated on three months ago. When mean diopter distribution charts are prepared to cover the temporally delimited groups, the charts indicate numerically any tendencies toward astigmatism over time. The results are used to evaluate the effectiveness of the surgical operations performed.

Even though the mean values are 41, 40, 41, 42, 43, etc. which appear to be fairly stable and close to the normal value, they are not sufficient to determine if the values of each point p on the cornea actually center on the mean value thereof (i.e., if the maximum and minimum values are close or dispersed). How far or how little the mean diopters are dispersed is verified by preparing a standard deviation matrix. The CPU 1 calculates standard deviation Sij on each of the 5,760 components constituting the N position matrices [Aij] regarding N patients. This provides a standard deviation matrix [Sij] shown in Table 7 below. .pa

TABLE 7

| 0.5 | 1.0 | 1.5 | 2.0 |
|---|---|---|---|
| 2.5 | 3.0 | 3.5 | 4.0 |
| . | | | |
| . | | | |
| 2.0 | 1.5 | | 1.0 |

How Table 7 is created will now be described in more detail. Different patients are measured for their diopter values at the same i-th point p on their cornea maps. It is assumed here that the first patient has a diopter value D1i; the second patient, D2i; the third patient, D3i, ... the N-th patient, Dni. The results are turned into the arithmetic mean $\Sigma Dni/N = gi$ regarding the same point p on the cornea map. There are N components for the i-th point p on the N patient's cornea maps. The variables of the same point p for the individual patients are assumed to be D1i, D2i, D3i, ..., Dni. The deviation between each variable and the mean value gi is doubled for all variables, and the results are added up to form the following variation (i.e., deviation-squared sum):

$$Sa = (D1i - gi)^2 + (D2i - gi)^2 + (D3i - gi)^2 \ldots, + (Dni - gi)^2$$

The variation Sa is divided by N to acquire a mean value, whereby the following variance is obtained:

$$\begin{aligned} Sb &= Sa/N \\ &= ((D1i - gi)^2 + (D2i - gi)^2 + (D3i - gi)^2 \ldots, + (Dni - gi)^2)/N \end{aligned}$$

When the square root of the above variance Sb is obtained, the following standard deviation Si is provided:

$$\begin{aligned} \text{Standard deviation } Si &= \sqrt{(Sb)} \\ &= \sqrt{((D1i - gi)^2 + (D2i - gi)^2 + (D3i - gi)^2 \ldots, + (Dni - gi)^2)/N} \end{aligned}$$

Since the above is the standard deviation regarding one matrix component, the general standard deviation matrix for the 5,760 components constituting the position matrix [Aij] is defined as [Sij]. For each of the N patients, 5,760 arithmetic mean values $\Sigma DNi/N = gi$ are acquired from the medical record file 31 comprising N pages. The mean value matrix $\Sigma[Dij/N]$ of Table 5 may be used as the 5,760 gi values.

In other words, for each of the components in the position matrix [Aij] covering the N patients, the CPU 1 inserts diopter values D1i, D2i, D3i, ..., Dni and the mean value gi into the standard deviation formula $$Si = \sqrt{(Sb)}$$

in order to calculate the standard deviation Si. In this manner, the standard deviation Si is obtained for each of the 5,760 components. The results are summarized as one standard deviation matrix [Sij] in Table 7. This matrix is stored in the form of numeric data on the hard disc 8.

Figure 8:
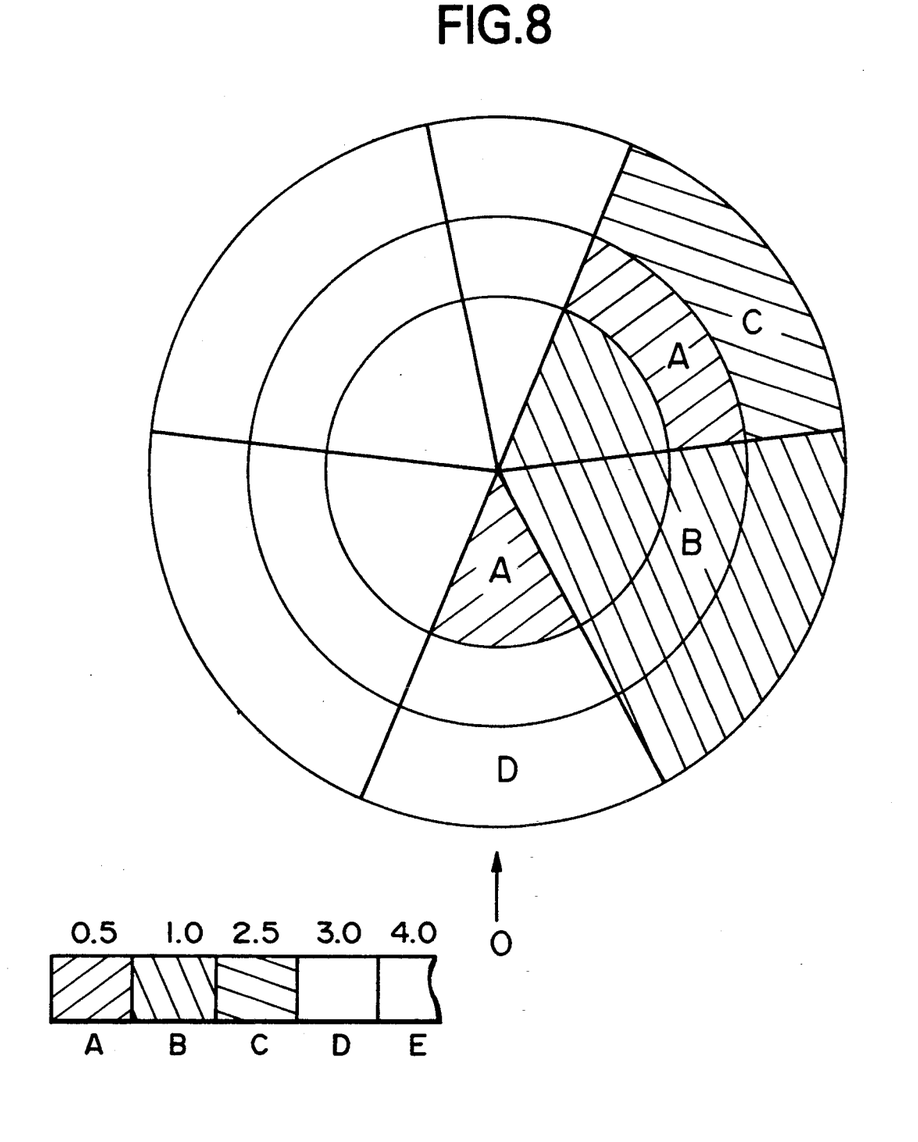
FIG. 8 is a distribution chart showing a standard deviation matrix using color pallets according to the invention.

Using color pallets of FIG. 8, the CPU 1 then expresses on the cornea map of FIG. 3 the value of each of the components constituting the diopter standard deviation matrix [Sij]. The representation is given in color on the CRT 3. In FIG. 8, the component values of the standard deviation matrix [Sij] are shown in different colors: value 0.5 in color code A, value 1.0 in color code B, value 2.5 in color code C, value 3.5 in color code D, value 4.0 in color code E, and so on. Although the component values of the mean standard deviation matrix [Sij] are given here in units of 0.5 for the sake of simplicity, these values may alternatively be given in smaller units such as 0.25 (i.e., 0.25, 0.5, 0.75, 1.0, etc.) using an increased number of color pallets. Another alternative is to represent the values using graphic patterns composed of points and shadings instead of color pallets. In this manner, the overall distribution chart showing the standard deviation matrix [Sij] is obtained over the cornea map, as illustrated in FIG. 8.

Medical records similar to those of the patients are also taken of a group of ophthalmologically normal people having twenty-twenty vision on average, and a distribution chart of the standard deviation matrix [Sij] is also prepared regarding these people with normal eyesight. As is the case with the charts of FIGS. 6 and 7, the distribution chart of the patients' standard deviation matrix [Sij] is compared with that of the normally sighted people's to evaluate the surgical techniques employed for later improvement. Furthermore, the comparative evaluation offers post-operative explanations of high educational value to interns.

Distribution charts of the standard deviation matrix [Sij] may also be prepared about the same group of patients by temporally dividing them into a number of groups, i.e., according to the elapsed time following the operation. Typically, the patients are divided into a group of patients operated on the day before, a group of patients operated on one week ago, a group of patients operated on one month ago, and a group of patients operated on three months ago. The distribution charts thus prepared indicate numerically any tendencies of the patients toward astigmatism over time.

Figure 9:
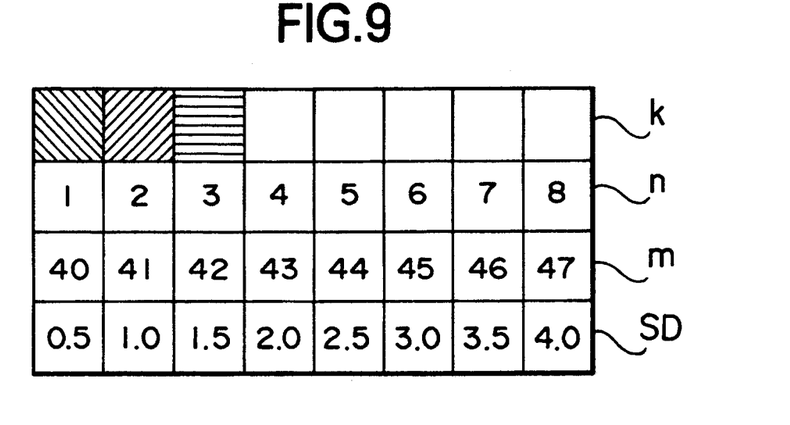
FIG. 9 is a table listing color codes, sample (mean) counts, diopter mean values and standard deviation values, all shown in a mutually associated manner according to the invention.

FIG. 9 lists color codes (already discussed) of a color pallet k, sample (mean) counts n, diopter mean values m and standard deviation values SD, all shown in a mutually associated tabular manner. These data and their combinations are predetermined and stored on the hard disc 8. The combinations of the data in FIG. 9 may be rearranged and may be displayed as needed on the CRT 2 by use of a read instruction.

Figure 10:
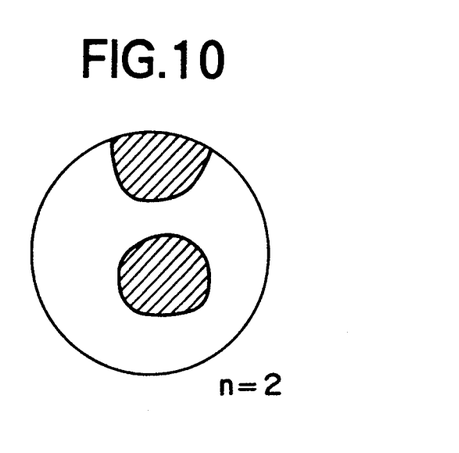
FIG. 10 is a view showing a sample count (mean) distribution chart.
Figure 11:
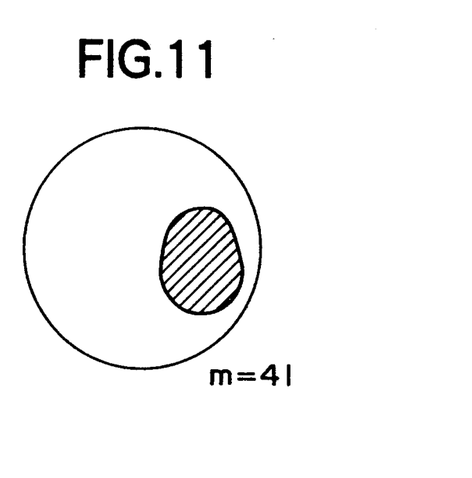
FIG. 11 is a view showing a diopter mean value distribution chart.
Figure 12:
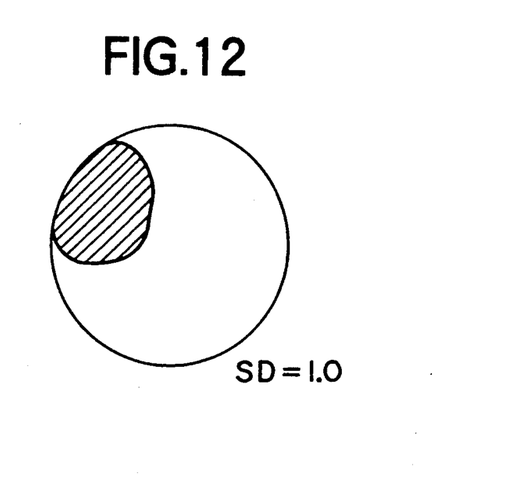
FIG. 12 is a view showing a standard deviation distribution chart.

FIGS. 10 to 12 are a set of views showing illustratively a sample count (mean) distribution chart, a diopter mean value distribution chart and a standard deviation distribution chart as they are displayed on the CRT 2. FIG. 10 is the sample count (mean) distribution chart provided by painting in the applicable color those sets of points p for which the sample (mean) count n in FIG. 9 is 2. FIG. 11 is the diopter mean value distribution chart furnished by painting in the applicable color code a set of points p for which the diopter mean value m in FIG. 9 is 41. FIG. 12 is the component value distribution chart of the standard deviation matrix [Sij] obtained by painting in the applicable color code a set of points p for which the standard deviation SD in FIG. 9 is 2.

When two groups of patients having undergone different surgical procedures are compared in terms of the sample (mean) count n, diopter mean value m and standard deviation SD, it is possible to code in color which areas of the two groups have significant differences therebetween.

For display purposes, the sample (mean) counts, diopter mean values and standard deviation values may be edited as desired after retrieval from the hard disc 8. The newly edited data may be displayed in diverse forms on the CRT screen.

As described, the method for displaying the optical properties of corneas according to the invention involves a number of steps. First a plurality of data matrices are generated about a plurality of corneas having different conditions. An arithmetic mean value of each of the components constituting the data matrices is calculated so as to prepare a mean value matrix. That mean value matrix is displayed in relevant positions on the cornea map using any of color pallets and graphic patterns associated with the mean value of each of the components. In addition, a standard deviation of each of the components is calculated using the mean value matrix and the data matrices so as to prepare a standard deviation matrix. That standard deviation matrix is displayed in relevant positions on the cornea map using any of color pallets and graphic patterns associated with the standard deviation of the components. This method represents in numerical terms the tendencies to astigmatism of a given group of patients over time after their cornea operations. Comparing and studying distribution charts of matrix components between patients and normally sighted people offers valuable evaluation of the surgical techniques employed. The method also makes it possible to provide a comprehensive representation of numerous patients' tendencies of eyesight recovery following their operations or a particular patient's tendency of eyesight recovery over time. Furthermore, the method serves as a valuable tool for giving post-operative explanations to interns.

As many apparently different embodiments of this invention may be made without departing from the spirit and scope thereof, it is to be understood that the invention is not limited to the specific embodiments thereof except as defined in the appended claims.

What is claimed is:

1. In a method for displaying optical properties of corneas comprising the steps of:
    establishing a cornea map by dividing a cornea of a three-dimensional shape into a plurality of minute areas in a predetermined coordinate system;
    establishing a pseudo-two-dimensional position matrix corresponding to said minute areas and made of a plurality of components;
    having a cornea analyzer measure the optical properties of said minute areas to generate data matrices corresponding to the components constituting the position matrix; and
    displaying said data matrices in relevant positions on said cornea map using any of color pallets and graphic patterns associated with the data values involved;
    the improvement comprising the steps of:
    generating a plurality of data matrices about a plurality of corneas having different conditions;
    calculating an arithmetic mean value of each of the components constituting said data matrices so as to prepare a mean value matrix; and
    displaying said mean value matrix in relevant position on said cornea map using any of color pallets and graphic patterns associated with the mean value of each of said components.

2. In a method for displaying optical properties of corneas comprising the steps of:
    establishing a cornea map by dividing a cornea of a three-dimensional shape into a plurality of minute areas in a predetermined coordinate system;
    establishing a pseudo-two-dimensional position matrix corresponding to said minute areas and made of a plurality of components;
    having a cornea analyzer measure the optical properties of said minute areas to generate data matrices corresponding to the components constituting the position matrix; and
    displaying said data matrices in relevant positions on said cornea map using any of color pallets and graphic patterns associated with the data values involved;
    the improvement comprising the steps of:
    generating a plurality of data matrices about a plurality of corneas having different conditions;
    calculating an arithmetic mean value of each of the components constituting said data matrices so as to prepare a mean value matrix;
    calculating a standard deviation of each of said components using said mean value matrix and said data matrices so as to prepare a standard deviation matrix; and
    displaying said standard deviation matrix in relevant positions on said cornea map using any of color pallets and graphic patterns associated with the standard deviation of each of said components.

* * * * *